United States Patent
Tziviskos et al.

[11] Patent Number: 6,011,993
[45] Date of Patent: Jan. 4, 2000

[54] METHOD OF MAKING IMPLANTED CERAMIC CASE WITH ENHANCED CERAMIC CASE STRENGTH

[75] Inventors: George Tziviskos, Woodland Hills, Calif.; Tom J. Law, Tempe, Ariz.

[73] Assignee: Advanced Bionics Corporation, Sylmar, Calif.

[21] Appl. No.: 09/280,179

[22] Filed: Mar. 29, 1999

Related U.S. Application Data

[60] Provisional application No. 60/083,823, Apr. 30, 1998.

[51] Int. Cl.⁷ .................................................. A61N 1/375
[52] U.S. Cl. ................................................................ 607/36
[58] Field of Search .............................. 607/1, 2, 36–38; 174/17.05, 17.08, 50.3, 52.3

[56] References Cited

U.S. PATENT DOCUMENTS

| | | |
|---|---|---|
| 4,532,930 | 8/1985 | Crosby et al. . |
| 4,991,582 | 2/1991 | Byers et al. . |
| 5,095,904 | 3/1992 | Seligman et al. . |
| 5,776,172 | 7/1998 | Schulman et al. . |
| 5,782,891 | 7/1998 | Hassler et al. ............................ 607/36 |

*Primary Examiner*—William E. Kamm
*Assistant Examiner*—George R. Evanisko
*Attorney, Agent, or Firm*—Bryant R. Gold

[57] ABSTRACT

An implantable medical device is made from an electronic subassembly hermetically sealed in a ceramic case filled with a potting material. Use of the potting material enhances the capacity of the device to withstand mechanical shock without failure. The device includes a hollow ceramic or other case having an open end to which a metal ring is hermetically bonded. The inside surface of the ceramic case is treated (cleansed and activated) to assure the potting material adheres to it. The potting material, while in a non-cured fluid or quasi-fluid state, is inserted inside of the ceramic case. The electronic circuitry is next inserted into the open end of the ceramic case while the potting material is still in a non-cured, soft or fluid state. The electronic circuitry displaces some of the potting material and the potting material fills the voids between the electronic circuitry and the ceramic case. The potting material is then slowly cured, and once cured, supports the walls of the ceramic case and protects the electronic circuitry embedded therein. A header (to which the electronic circuitry is attached) is hermetically bonded to the metal band on the open end of the ceramic case, thereby hermetically sealing the implantable device.

9 Claims, 2 Drawing Sheets

METHOD OF MAKING IMPLANTED CERAMIC CASE WITH ENHANCED CERAMIC CASE STRENGTH

CROSS REFERENCE TO RELATED APPLICATIONS

This application claims the benefit of U.S. Provisional Application Ser. No. 60/083,823, filed Apr. 30, 1998.

BACKGROUND OF THE INVENTION

The present invention relates to a structure and method of manufacture of a ceramic case for implantation in a living body, and more particularly to a ceramic case that has enhanced strength due to the use of a potting material or encapsulant to support the ceramic walls of the ceramic case.

Electronics packages that are implanted in living bodies must be housed in packages constructed of biocompatible materials. These packages must protect the electronic circuitry located within them from body fluids and ions so that the electronic circuitry can survive for extended periods of time without any significant changes in performance.

Today, the most commonly used metals for implantable packages are titanium, stainless steel and cobalt-chromium alloys. These metals are biocompatible and corrosion resistant. Normally, the package construction consists of parts that are welded together to insure hermeticity. However, where there is a need to inductively couple an alternating electromagnetic field to an internal pickup coil, the metal package becomes a hindrance. Such is the case for an implanted stimulator that is powered from an external source. Specifically, transmission of power is substantially reduced by eddy currents generated in the metal package due to the alternating electromagnetic field. To solve that problem, receiving coils may be placed on the outside of the metal package, increasing the size and complexity of the implanted device.

Glass and ceramic material represent viable materials for an implantable medical device package because they are transparent to alternating electromagnetic fields. Receiving coils can be placed inside a hermetic zone of a ceramic or glass package, creating an overall smaller and simpler implant device and reducing the possibility of coil failure due to saline leakage. Advantageously, glasses and ceramics are inert and highly insoluble, which are favorable characteristics for long term implant materials.

Unfortunately, ceramics and glasses are inelastic and fragile when subjected to tensile stresses such as the stresses generated under mechanical shock or impact. Additionally, they are subject to fracture not only from mechanical shock but also from differential thermal expansion if even a moderate temperature gradient exists thereacross. Therefore, welding is not a practical method of sealing glass or ceramic materials. Instead, if a ceramic package is used, virtually the entire package and its contents must be raised to the high melting temperature of the ceramic or metal braze that is used to effect a sealing of the ceramic package. Such high-temperature sealing methods are unsatisfactory.

One type of hermetically sealed ceramic and metal package is shown in U.S. Pat. No. 4,991,582, issued to Byers et al. and incorporated herein by reference. A ceramic case and a metal band are hermetically sealed together, each being characterized by similar coefficients of linear thermal expansion. The electronic circuitry is then loaded inside the package, and final package closure is effected by welding a metal header plate to the metal band. Disadvantageously, the electronic circuitry is unsupported and is thus susceptible to damage from an impact force.

In view of the above, it is evident that what is needed is a ceramic or other package that has improved mechanical impact resistance and can protect the electronic circuitry carried inside of the package.

BRIEF SUMMARY OF THE INVENTION

The present invention advantageously addresses the needs above as well as other needs by providing an implantable medical device, e.g., an implantable cochlear stimulator (ICS), having a ceramic or similar case that exhibits enhanced case strength.

The material, e.g., ceramic, from which the case of the present invention is made is inert to body fluids. The majority of the case is made of biocompatible ceramic material having an open end. Electronic circuitry and a selected potting material are placed inside of the case through the open end. A closed metal band or ring is then, e.g., welded, to the open end of the ceramic case. The metal band is made from a biocompatible material that has the same coefficient of thermal expansion (CTE) as the ceramic material. The attachment of the metal band to the ceramic case may be effectuated in any suitable manner, e.g., it can either be a butt joint or one of the components may have a fixturing ring or step for self jigging. The attachment of the metal band also provides a hermetic seal. The preferred method of attachment is brazing the metal band to the ceramic case using a metal or metal alloy braze. Advantageously, such brazing, while performed at a high temperature, may be done without the electronic circuitry being present.

An electronic circuit assembly (hereafter also referred to herein as "electronic circuitry", "circuitry", or "electronics") is sized to fit inside of the ceramic case. Prior to the insertion of the electronic circuit assembly into the ceramic case, the ceramic case is filled with a non-cured potting material that is in a fluid state. When cured, the potting material thereafter advantageously supports the fragile walls of the ceramic or other case and prevents such walls from collapsing under an impact or load. Moreover, the potting material also supports the electronic circuitry. The uncured potting material is initially soft, having the constituency of a high viscosity fluid (e.g., much like ketchup) to allow the electronic circuitry to be inserted into the ceramic case, displacing some of the potting material and allowing the potting material to fill the voids between the electronic circuitry and the inside walls of the ceramic case. Once the electronic circuit assembly is inside the ceramic case, the potting material cures, making it rigid. The header is then welded to the metal band, sealing the package. The header has a plurality of electrical connectors (electrical feed-through terminals) passing through it for connecting electrical leads of the electronic components inside of the package. Once thus assembled, the implantable electronic device within its ceramic (or other) case is ready to be implanted in a living body.

An added benefit provided by the invention is that the potting material acts as a trap or collector for any moisture that might enter the hermetic package, thereby preventing condensation of moisture on the microcircuits and other delicate components that form part of the electronic circuitry. Such moisture trap or collector thus extends the useful life of the device.

BRIEF DESCRIPTION OF THE DRAWINGS

The above and other aspects, features and advantages of the present invention will be more apparent from the following more particular description thereof, presented in conjunction with the following drawings wherein.

Figure 1:
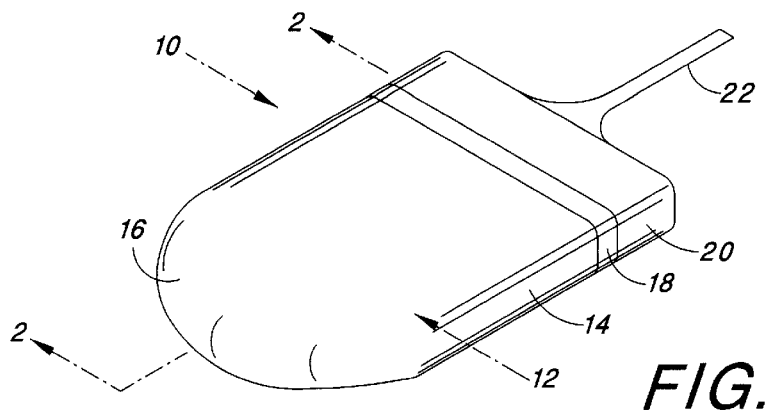
FIG. 1 is a perspective view of a ceramic package of the type that may be used with the present invention.

For the convenience of the reader, below is a list of reference numbers associated with the figures.

| Ref. No. | Component |
| --- | --- |
| 10 | Implantable Electronic Device |
| 12 | Sealed Implantable Package |
| 14 | Ceramic Case |
| 16 | Closed End of Ceramic Case |
| 18 | Metal Band |
| 20 | Header |
| 22 | Cable |
| 24 | Open End of Ceramic Case |
| 25 | Permanent Magnet |
| 26 | Antenna Coil |
| 27 | Electronic Components |
| 28 | Potting Material |
| 30 | Electrical Connectors |
| 31 | Printed Circuit Board |
| 32 | Substrate assembly, e.g., printed circuit board loaded with electronic components |
| 34 | Header Plate |

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

For illustration purposes, the following description of the present invention is shown in conjunction with an implantable electronic package or device 10, shown in FIG. 1. The implantable electronic device 10 typically comprises a medical device that carries out a desired medical function, e.g., stimulation of the cochlea or other nerves. The device 10 comprises a sealed implantable package 12 including a case 14 having a closed end 16, a metal band 18 and a header 20 for closing the package. The case 14 may be made from a fragile material, i.e, a material that is relatively easily broken or cracked under stress or impact, such as the ceramic case disclosed in the previously-referenced '582 patent. It should be understood, however, that the case 14 could be made from other suitable implantable materials other than a fragile ceramic. A plurality of electrical leads in a cable 22 are connected to electronic or other components inside of the package 10 through electrical feed-through pins or terminals located in the header plate 34 (FIGS. 2, 3 and 4) of the header 20. These electronic or other components are configured in a desired circuit and/or mechanical relationship so that the device 10 is able to carry out its intended function, e.g., neuro-stimulation, sensing, monitoring, or the like.

Figure 2:
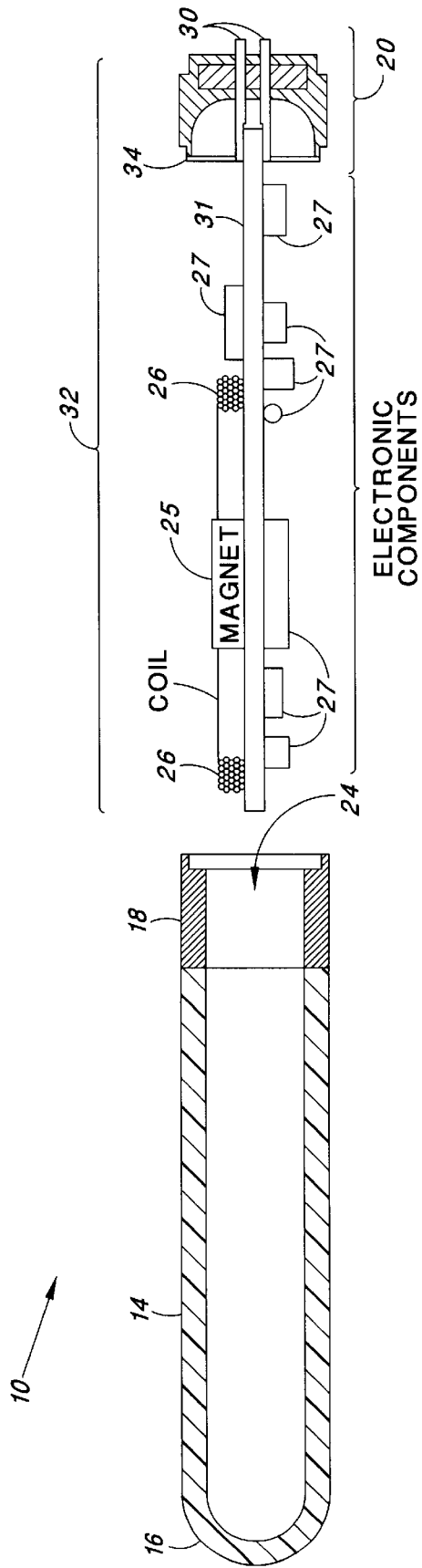
FIG. 2 is an exploded view of the main components of the invention, except for the potting material, prior to assembly of the invention.

FIG. 2 shows an exploded view of several of the principal components of the medical device 10. As seen in FIG. 2, device includes the case 14, a metal band or ring 18 and an electronic substrate assembly 32. The case has an open end 24 and a closed end 16. The closed end 16 is typically curved to avoid sharp corners. The metal ring or band 18 is hermetically attached around the open end 24 of the case 14, as taught in the '582 patent, or as is otherwise known in the art. The electronic circuit assembly 32 includes a circuit board 31 on which various individual electrical components 27 are mounted or otherwise carried. Some of the electronic circuitry may be formed within the circuit board 31. The electronic components 27 may include, e.g, a permanent magnet 25 and an antenna coil 26, as is known in the cochlear stimulation art. At least one of the electronic components typically comprises an integrated circuit (IC) chip. Others of the electronic components may include other IC chips, capacitors, resistors, inductors and the like. The circuit board 31 is affixed at one end to the header 20. The header 20 includes a header plate 34 which is configured to mate with the open edge of the metal band 18.

During assembly, a pre-measured amount of potting material 28 (not shown in FIG. 2) is placed inside of the case 14 while still in a non-cured or fluid state. The electronic substrate assembly 32 is next inserted into the potting-material-filled case, while the potting material is still in its non-cured or fluid state, displacing some of the potting material. The potting material inside of the case is then allowed to cure. Once the potting material has cured, the header plate 34 is welded to the metal band 18 in order to hermetically seal the device.

Figure 3:
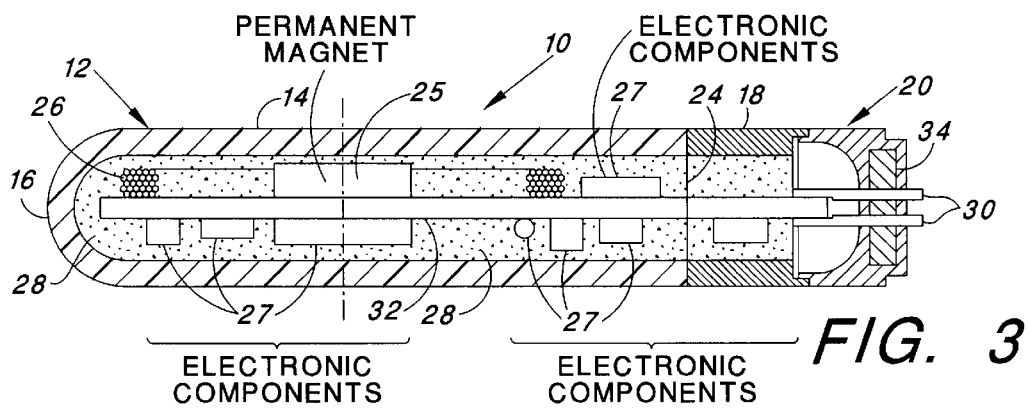
FIG. 3 is a longitudinal sectional view of the assembled package of FIG. 1 taken along line 2—2 in FIG. 1.
Figure 4:
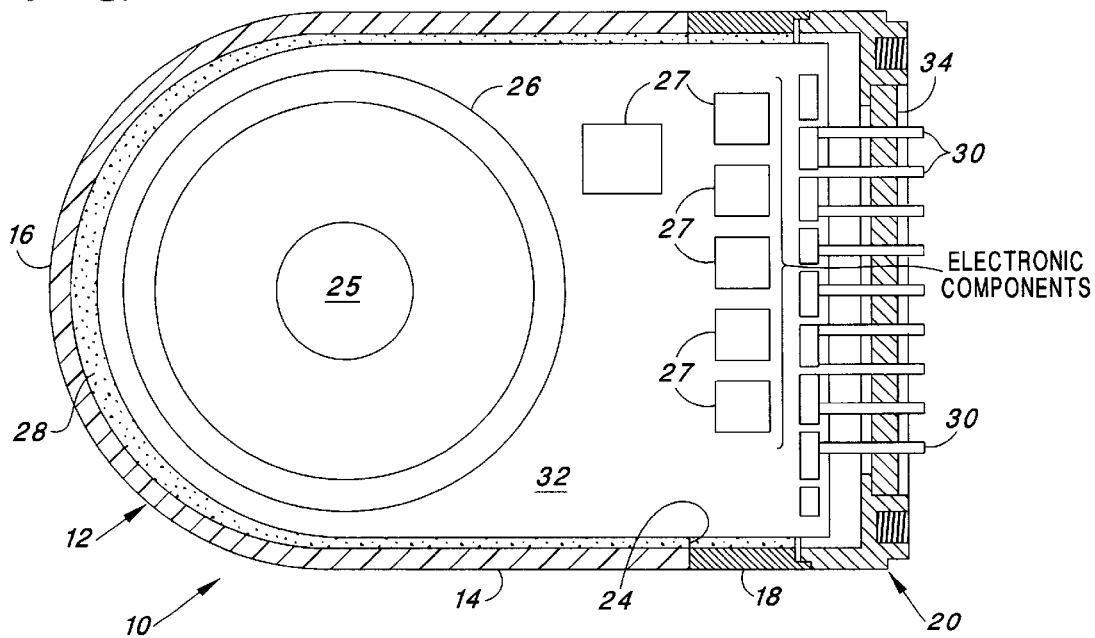
FIG. 4 is a sectional top view of the package taken along line 3—3 in FIG. 3.

Turning next to FIGS. 3 and 4, the assembled device 10 is illustrated in cross-section. The ceramic case 14 is preferably formed of a biocompatible ceramic material, e.g., Aluminum Oxide ($Al_2O_3$) or Zirconium Oxide ($ZO_2$), and most preferably from Zirconium Oxide with about 3% yttrium, having a coefficient of thermal expansion of about $7 \times 10^{-6}/°$ C. to $8 \times 10^{-6}/°$ C. One end of the ceramic case 14 comprises a closed end 16. The other end of the case comprises an open end 24. The open end 24 opens into a cavity within the ceramic case. It is through this open end 24 that the electronic substrate assembly 32, e.g., a printed circuit board loaded with electronic components 27, is received into the cavity inside of the case. Some of these electronic or electrical components 27 may be susceptible to impact or vibration damage. Some or all of these electronic or electrical components 27 may also be susceptible to damage or malfunction when exposed to moisture condensation. Typically, as mentioned above in connection with FIG. 2, one of the components comprises an antenna coil 26, and another comprises a permanent magnet 25. The coil 26 is used for receiving and/or transmitting electromagnetic energy (e.g., electrostatic energy and/or radio frequency energy) from an external coil. The magnet 25 is used to help align and maintain alignment between the external coil and implanted coil 26.

Advantageously, the use of a ceramic material for at least a portion of the case facilitates the transfer of energy through the walls of the case without serious degradation or attenuation. In turn, this prevents absorption of such energy within the case walls, and hence prevents undesirable heat generation within the case walls.

At the open end 24 of the case 14 is the metal band 18. This band 18 is attached to the ceramic case 14. The metal band 18 should be formed of a metal having a coefficient of thermal expansion substantially the same as the ceramic material forming the ceramic case 14. Typically, the band 14 is made from a biocompatible metal, e.g. titanium, stainless steel and cobalt-chromium alloys, and preferably from an alloy of Titanium-45 Niobium (i.e., 55% Ti and 45% Nb), having coefficient of linear thermal expansion on the order of between about $6 \times 10^{-6}/°$ C. to $8 \times 10^{-6}/°$ C. Note that both the Zirconium oxide and the Titanium-45 Niobium have similar coefficients of thermal expansion (CTE). This minimizes the risk of cracking when the ceramic case 14 and metal band 18 are bonded together at high temperatures and then cooled.

The bonding of the band 18 to the ceramic case 14 may be done with a butt brazing technique using a metal or metal alloy of nickel and titanium braze. Since these braze bonding methods are done at very high temperatures that could potentially damage the electronic circuit components 27 on the substrate assembly 32, the substrate assembly 32 and its electronic circuitry is inserted into the ceramic case only after the attachment of the metal band 18 has been completed.

The ceramic case 14 may be formed to any desired shape and dimension by processes known to those skilled in the art of ceramic formation. Likewise, known processes may be utilized to bond the band 18 to the open end 24 of the ceramic case 14 utilizing biocompatible sealing materials. The substrate assembly 32 carries electronic and other components 25, 26, 27 and is connected to the header 20. The header 20 is welded to the band 18 when the implantable electronic package 10 is finally closed.

The header 20 closes and hermetically bonds to the band 18. The header 20 carries a plurality of electrical feed-through connectors 30 for connecting to the substrate 32 housed within the ceramic case 14. The feed-through connectors 30 thus provide a means for making electrical connection with the electronic circuitry mounted on or formed within the substrate assembly 32. The feed-through connectors 30 are hermetically sealed to and extend through a header plate 34. In addition, the header assembly 20 preferably supports the substrate assembly 32 upon which the electronic and other components 25, 26 and 27 are mounted or carried. As shown in FIGS. 3 and 4, the substrate assembly 32 extends through the open end 24 of the ceramic case 14, and typically has electronic or other components mounted on both sides of the circuit board 31. Ideally, the coil antenna 26 is positioned away from any metal components (i.e., the band 18 and header 20) so as to minimize interference when sending and/or receiving signals.

As seen from FIGS. 2, 3 and 4, the ceramic case 14 comprises a thin shell having a cavity on the inside. The side wall of the case 14 is approximately 0.020 to 0.050 inches thick. Because ceramic material may be very fragile, any mechanical impact or shock to the shell may break or crack it, thus breaking, opening or compromising the hermetic seal. Should the ceramic case 14 break or crack while implanted, the electronic components would be exposed to body fluids and would likely fail after a short exposure period to such fluids. In addition, the body tissue within which the device is implanted could have an adverse reaction to the components inside of the case.

The present invention strengthens the ceramic case 14 and prevents it from breaking or cracking by inserting a potting material 28 into the ceramic case 14. This potting material 28 fills all (or most all) of the voids within the cavity inside of the case and provides support for the case walls. Thus, the potting material 28 prevents the ceramic case 14 from collapsing under impact. Further, the potting material 28 effectively reduces flexure of the walls, preventing stresses from reaching critical limits. Additionally, the potting material 28 fills the voids around the electronic substrate assembly 32 and the wall of the ceramic case 14, thus supporting the substrate assembly 32 and protecting it (and the electronic components mounted or formed thereon) from impact or vibration forces. Moreover, the potting material also functions as a trap or collector for any moisture that may enter the hermetic package, thereby preventing condensation of such moisture on the electrical components, and thereby extends the useful life of the implantable device.

Many types of materials may be used as the potting material 28 to fill the voids and strengthen the ceramic case 14. Many different commerically-available potential potting materials have been tested to determine the increase in mechanical strength of the ceramic case. Some of the potential potting materials do not appear to improve case strength significantly, such as RTV3140, urethane (Burtin PC13), urethane foam (Burtin 500), silicone elastomer (Dow Coming 170) and $Al_2O_3$-filled epoxy (Cotronics 801). Moreover, some of the potential potting materials exhibited significant shrinkage, (such as, Cotronics 801), thereby causing cracks and voids to form in the compound. Other potential potting materials passed impact testing where the ceramic case was tested to an impact force of approximately 150 lbs, and thus provide a satisfactory potting material for use with a ceramic case in accordance with the present invention. Some of the potting materials that have proven to be satisfactory are: (1) $Al_2O_3$-filled epoxy (Cotronics 780), (2) urethane (Conap UC48), (3) epoxy (Master-Bond EP21LV & EP30 and Grace Stycast 1276), and (4) epoxy (e.g., Master-Bond EP21LV & EP30 and Grace Stycast 1276) containing various benign filler materials. As used in this context, "benign" refers to filler materials that are substantially inert relative to the epoxy material, and which do not adversely affect the performance of the electronic circuitry carried within the medical device. Examples of a suitable benign filler material include: alumina ($Al_2O_3$) powder, zirconia ($ZO_2$) powder, or ruby beads.

The cure temperature of the selected potting material 28 is another important consideration. Potting materials 28 can vary in cure temperatures from room temperature (23–27° C.) to elevated temperatures (>100° C.). Tests performed to date have shown that potting materials that cure at elevated temperatures have a tendency to shrink when cooled back to room temperatures. Because of this, it is important that the elevated-temperature-cure materials have a similar thermal coefficient of expansion as the ceramic case material. If the potting material 28 shrinks too quickly, or at a different rate than the ceramic case 14, the walls of the ceramic case 14 may crack. Also, some of the potting materials 28 may expel or give off moisture during curing or become sources of ionic contamination. Such effects on the long-term performance on the implantable device must thus be considered when selecting a suitable potting material.

Tests have shown that good adhesion between the potting material 28 and the ceramic case 14 is beneficial. To promote such adhesion, the ceramic case should be cleaned and its surface treated prior to insertion of the potting material. Such cleaning and surface treating is preferably performed by immersing the ceramic case in an ultrasonic bath of a suitable cleaning solution, e.g., alcohol mixed with water, to remove surface contamination. After immersion in the ultrasonic bath for a suitable time period, e.g., 20±10 minutes, the ceramic case is dried and then subjected to plasma etching in order to activate the surface of the ceramic. The plasma etching may be performed for 5 minutes (±10%) in an Oxygen gas, followed by 5 minutes (±10%) in an Argon gas.

From the tests performed to date, the preferred potting material 28 comprises a commerically-available epoxy material (HYSOL FP4651), or such an epoxy material containing a benign filler material. Such potting material (HYSOL FP4651) may be obtained commercially from, e.g., Dexter Electronics Materials Division, of The City of Industry, California.

As indicated above, the selected potting material 28, while in a non-cured, soft, or fluid state, is inserted into the open end 24 of the ceramic case 14. In such a non-cured state, the potting material acts like a high viscosity liquid, and is thus displaced as the electronic substrate assembly 32, with its electronic and other components 25, 26, 27, and 31, is inserted into the open end 24 of the ceramic case 14.

Once the subassembly 32 has been inserted into the non-cured-potting-material-filled case, the potting material 28 is cured at the manufacturer's recommended schedule so as to produce minimum shrinkage. When commerically-available epoxy such as HYSOL FP4651 is used as the potting material 28, the epoxy is cured by heating the assembly to approximately 110° C. (±11° C.) for approximately one hour (±6 minutes), followed by a post cure at approximately 165° C. (±17° C.) for approximately 3 hours (±18 minutes). This cure schedule advantageously reduces shrinkage and guarantees the epoxy will exhibit a sufficiently high glass transition temperature ($T_g$) for subsequent processing of the package. That is, a high glass transition temperature minimizes thermal-induced stresses. The assembly is then slowly cooled down to room temperature over a period of approximately 8 hours (±48 minutes). Moisture escapes from the open end 24 during the cure cycle. The header 20 is then laser welded to the metal band, sealing the package.

Tests performed with the cured-epoxy potting material 28 inside of the ceramic case 14 have verified that the case 14 is able to withstand an increase in the mechanical impact shocks before damage to the case. For example, all units tested (with cured potting material therein) successfully withstood an impact of at least 4.38 joules.

It is significant that the cured potting material 28 also prevents the electronic circuitry mounted on or formed within the substrate assembly 32 from moving or vibrating, thus decreasing the incidence of vibration failure. Hence, once assembled, it is seen that the implantable electronic package 10 exhibits enhanced ceramic case strength, and provides a safe and reliable housing for the delicate electronic circuitry carried therein.

While the invention herein disclosed has been described by means of specific embodiments and applications thereof, numerous modifications and variations could be made thereto by those skilled in the art without departing from the scope of the invention set forth in the claims. For example, the ceramic case may also be used to house or protect other types of assemblies, in addition to electronic circuit assemblies.

For example, a potting-material-filled ceramic housing may be used to protect an implantable hydraulic assembly, or an implantable electromechanical pump (e.g., an insulin pump), in which certain components need to be protected from the environment within the human or other body. Such assemblies may communicate with external components via a header assembly as described above which has hermetic feed-through posts, e.g., hermetic pipettes for communicating a fluid to an electromechanical pump and/or hermetic electrical feed-through terminals for making electrical connection with electronic circuitry.

What is claimed is:

1. A method of strengthening a case in which an implantable medical device is hermetically sealed, comprising the steps of:

(a) providing a case having a cavity therein and an open end through which the cavity is accessible;

(b) placing a metal band on the open end of the case, the case and metal band being matable;

(c) hermetically sealing the case and metal band together forming a housing structure;

(d) inserting a potting material while in a fluid state into the open end of the housing structure so as to substantially fill the cavity;

(e) inserting a component assembly into the open end of the structure so as to be immersed within the fluid potting material within the cavity; the potting material thereby filling voids within the cavity between the component assembly and the housing structure;

(f) curing the potting material; and (g) hermetically sealing a header to the metal band of the housing structure, thereby forming an hermetically sealed implantable device, the header having a plurality of hermetically sealed feed-through posts that provide external communication with the component assembly sealed within the device.

2. The method of claim 1 wherein the step of inserting the potting material while in a fluid state into the open end of the housing structure comprises:

forming a fluid potting material from the group of potting materials consisting of urethane, urethane foam, silicone, epoxy, epoxy filled with at least one benign material, and $Al_2O_3$-filled epoxy;

cleaning and activating an inside surface of the cavity; and inserting the fluid potting material into the cavity so as to substantially fill the cavity.

3. The method of claim 1 wherein the step of curing the potting material comprises maintaining the potting material at a first elevated temperature for a first time period, followed by maintaining the potting material at a second elevated temperature for a second time period, followed by slowly cooling the potting material to room temperature over a third time period.

4. The method of claim 3 wherein the potting material consists essentially of epoxy.

5. The method of claim 3 wherein the potting material consists essentially of a mixture of epoxy and alumina powder.

6. The method of claim 3 wherein the first elevated temperature comprises approximately 110° C. and the second elevated temperature comprises approximately 165° C.

7. The method of claim 6 wherein the first time period comprises approximately one hour, the second time period comprises approximately three hours, and the third time period comprises approximately 8 hours.

8. The method of claim 1 wherein step (g) of hermetically sealing the header to the metal band comprises laser welding the header to the metal band.

9. The method of claim 2 wherein the step of cleaning and activating the inside surface of the cavity comprises immersing the case in an ultrasonic bath for at least five minutes, removing the case from the bath and drying it, and then plasma etching the inside surface of the cavity by exposing it to an Oxygen gas for a first exposure period, followed by exposing it to an Argon gas for a second exposure period.

* * * * *